United States Patent [19]
Yang et al.

[11] Patent Number: 6,120,847
[45] Date of Patent: Sep. 19, 2000

[54] SURFACE TREATMENT METHOD FOR STENT COATING

[75] Inventors: Dachuan Yang, Plymouth; Carmen Jacob, Anoka; Lixiao Wang, Maple Grove, all of Minn.

[73] Assignee: SciMed Life Systems, Inc., Maple Grove, Minn.

[21] Appl. No.: 09/226,930

[22] Filed: Jan. 8, 1999

[51] Int. Cl.⁷ .................................. B05D 3/00; B05D 3/04
[52] U.S. Cl. ......................... 427/335; 427/2.1; 427/2.24; 427/2.3
[58] Field of Search .................................. 427/335, 336, 427/2.24, 2.28, 2.1, 2.12, 2.3, 2.31

[56] References Cited

U.S. PATENT DOCUMENTS

| | | | |
|---|---|---|---|
| 2,282,274 | 5/1942 | Weiswasser et al. | 427/2.31 |
| 3,525,634 | 8/1970 | Elkind et al. | 427/335 |
| 3,527,650 | 9/1970 | Block | 427/2.31 |
| 3,676,171 | 7/1972 | Spiller et al. | 427/335 |
| 3,684,553 | 8/1972 | Van Dyk | 427/335 |
| 3,737,499 | 6/1973 | Kamena | 427/335 |
| 4,027,676 | 6/1977 | Mattei | 427/2.31 |
| 4,302,418 | 11/1981 | Cullis et al. | 427/335 |
| 4,391,797 | 7/1983 | Folkman et al. | 424/19 |
| 4,459,317 | 7/1984 | Lambert | 427/2 |
| 4,487,808 | 12/1984 | Lambert | 428/423.1 |
| 4,525,409 | 6/1985 | Elesh | 427/2.31 |
| 4,768,507 | 9/1988 | Fischell et al. | 128/303 R |
| 4,770,664 | 9/1988 | Gogolewski | 623/66 |
| 4,923,464 | 5/1990 | DiPisa, Jr. | 606/195 |

(List continued on next page.)

FOREIGN PATENT DOCUMENTS

| | | |
|---|---|---|
| 0 274 846 B1 | 7/1988 | European Pat. Off. . |
| 0 294 905 A1 | 12/1988 | European Pat. Off. . |
| 0 470 246 B1 | 2/1992 | European Pat. Off. . |
| 0 470 569 A1 | 2/1992 | European Pat. Off. . |
| 0 543 653 A1 | 5/1993 | European Pat. Off. . |
| 0 551 182 A1 | 7/1993 | European Pat. Off. . |
| 0 567 816 A1 | 11/1993 | European Pat. Off. . |
| 0 568 310 A1 | 11/1993 | European Pat. Off. . |
| 0 604 022 A1 | 6/1994 | European Pat. Off. . |
| 0 623 354 A1 | 11/1994 | European Pat. Off. . |
| 0 706 376 B1 | 4/1996 | European Pat. Off. . |
| WO 90/01969 | 3/1990 | WIPO . |

(List continued on next page.)

OTHER PUBLICATIONS

Bartoli et al., "In Vitro and In Vivo Antitumoral Activity of Free, and Encapsulated Taxol", *J. Microencapsulation*, vol. 7, No. 2, 1990, pp. 191–197.

Cox, David A., M.D. et al., "Effect of Local Delivery of Heparin and Methotrexate on Neointimal Proliferation in Stented Porcine Coronary Arteries", *Coronary Artery Disease*, vol. 3, No. 3, Mar. 1992, pp. 237–248.

Cox, D. A. et al., "Local Delivery of Heparin and Methotrexate Fails to Inhibit In Vivo Smooth Muscle Cell Proliferation", *Supplement to Circulation Abstracts From the 64th Scientific Sessions*, vol. 84, No. 4, Abstract No. 0284, 1991, p. II–71.

(List continued on next page.)

*Primary Examiner*—Diana Dudash
*Attorney, Agent, or Firm*—Crompton, Seager & Tufte, LLC

[57] ABSTRACT

A method is provided for eliminating surface imperfections on a medical device having a drug release coating including a therapeutic substance in a polymeric carrier disposed on at least a portion of the medical device. The medical device is preferably a stent including wire-like members interconnected to form struts with open interstices therebetween. A therapeutic substance incorporate into a polymeric carrier is disposed on the surface of the stent through which process imperfections including polymeric fibers, polymeric particles or other polymeric surface aberrations or imperfections are formed. This imperfections are eliminated by contacting the polymeric coating with a vaporized solvent for a specified period of time.

25 Claims, 2 Drawing Sheets

U.S. PATENT DOCUMENTS

| | | | |
|---|---|---|---|
| 4,969,890 | 11/1990 | Sugita et al. | 606/192 |
| 4,994,071 | 2/1991 | MacGregor | 606/194 |
| 5,019,096 | 5/1991 | Fox, Jr. et al. | 623/1 |
| 5,092,885 | 3/1992 | Yamada et al. | 623/11 |
| 5,102,417 | 4/1992 | Palmaz | 606/195 |
| 5,222,971 | 6/1993 | Willard et al. | 606/158 |
| 5,282,823 | 2/1994 | Schwartz et al. | 606/198 |
| 5,304,121 | 4/1994 | Sahatjian | 604/53 |
| 5,380,299 | 1/1995 | Fearnot et al. | 604/265 |
| 5,383,928 | 1/1995 | Scott et al. | 623/1 |
| 5,419,760 | 5/1995 | Narciso, Jr. | 604/8 |
| 5,423,885 | 6/1995 | Williams | 623/1 |
| 5,443,458 | 8/1995 | Eury | 604/891.1 |
| 5,443,496 | 8/1995 | Schwartz et al. | 623/1 |
| 5,447,724 | 9/1995 | Helmus et al. | 424/426 |
| 5,449,372 | 9/1995 | Schmaltz et al. | 606/198 |
| 5,449,382 | 9/1995 | Dayton | 623/1 |
| 5,464,650 | 11/1995 | Berg et al. | 427/2.3 |
| 5,512,055 | 4/1996 | Domb et al. | 604/265 |
| 5,514,154 | 5/1996 | Lau et al. | 606/195 |
| 5,527,337 | 6/1996 | Stack et al. | 606/198 |
| 5,545,208 | 8/1996 | Wolff et al. | 623/1 |
| 5,562,922 | 10/1996 | Lambert | 424/486 |
| 5,569,463 | 10/1996 | Helmus et al. | 424/426 |
| 5,569,469 | 10/1996 | Lovrecich | 427/335 |
| 5,578,075 | 11/1996 | Dayton | 623/1 |
| 5,591,227 | 1/1997 | Dinh et al. | 623/1 |
| 5,605,696 | 2/1997 | Eury et al. | 424/423 |
| 5,609,629 | 3/1997 | Fearnot et al. | 623/1 |
| 5,616,608 | 4/1997 | Kinsella et al. | 514/449 |
| 5,624,411 | 4/1997 | Tuch | 604/265 |
| 5,626,862 | 5/1997 | Brem et al. | 424/426 |
| 5,637,113 | 6/1997 | Tartaglia et al. | 623/1 |
| 5,651,986 | 7/1997 | Brem et al. | 424/484 |
| 5,660,873 | 8/1997 | Nickolaychik et al. | 427/2.31 |
| 5,674,241 | 10/1997 | Bley et al. | 606/198 |
| 5,674,242 | 10/1997 | Phan et al. | 606/198 |
| 5,679,400 | 10/1997 | Tuch | 427/2.14 |
| 5,697,967 | 12/1997 | Dinh et al. | 623/1 |
| 5,700,286 | 12/1997 | Tartaglia et al. | 623/1 |
| 5,716,981 | 2/1998 | Hunter et al. | 514/449 |
| 5,733,925 | 3/1998 | Kunz et al. | 514/449 |
| 5,755,769 | 5/1998 | Richard et al. | 623/11 |
| 5,776,184 | 7/1998 | Tuch | 623/1 |
| 5,779,732 | 7/1998 | Amundson | 606/198 |
| 5,837,008 | 11/1998 | Berg et al. | 623/1 |

FOREIGN PATENT DOCUMENTS

| | | |
|---|---|---|
| WO 90/13332 | 11/1990 | WIPO. |
| WO 91/07154 | 5/1991 | WIPO. |
| WO 91/10424 | 7/1991 | WIPO. |
| WO 91/11193 | 8/1991 | WIPO. |
| WO 91/12779 | 9/1991 | WIPO. |
| WO 92/00747 | 1/1992 | WIPO. |
| WO 92/12717 | 8/1992 | WIPO. |
| WO 92/15286 | 9/1992 | WIPO. |
| WO 93/06792 | 4/1993 | WIPO. |
| WO 93/11120 | 6/1993 | WIPO. |
| WO 94/21308 | 9/1994 | WIPO. |
| WO 96/03092 A1 | 2/1996 | WIPO. |
| WO 96/03984 | 2/1996 | WIPO. |
| WO 96/25176 | 8/1996 | WIPO. |
| WO 96/26689 | 9/1996 | WIPO. |
| WO 98/36784 | 8/1998 | WIPO. |

OTHER PUBLICATIONS

Dev, V. et al. "Kinetics of Drug Delivery to the Arterial Wall Via Polyurethane Coated Removable Nitinol Stent–Comparative Study of 2 Drugs", *Circulation Abstracts From the 66th Scientific Sessions*, vol. 88, No. 4, part 2, Abstract No. 1657, 1993, p. I–3.

Jampel, Henry D., M.D. et al., "In vitro Release of Hydrophobic Drugs From Polyanhydride Disks", *Ophthalmic Surgery*, dated prior to Jan. 8, 1991.

Lambert, T. et al., "A New Method For Arterial Drug Delivery Via Removable Stent", *JACC*, vol. 21, No. 2, Abstract No. 834–2, 1993, p. 483 A.

Lambert, T. et al., "Localized Arterial Drug Delivery From a Polymer Coated Removable Metallic Stent: Kinetics and Bioactivity of Forskolin", *Circulation Abstracts From the 66th Scientific Sessions*, vol. 88, No. 4, part 2, Abstract No. 1659, 1993, p. I–3.

Moses, Marsha A. et al., *Inhibitors of Angiogenesis*, Review, The Children's Hospital Medical Center, Boston, MA, dated prior to Jan. 8, 1999.

Pitt, C.G. et al., "The Design of Controlled Drug Delivery Systems Based on Biodegredable Polymers", *Progress in Contraceptive Delivery Systems*, M T P Press, Lancaster, 1980, pp. 17–18.

Tang, Chris et al., "Regression of Collagen–Induced Arthritis with Taxol, A Microtubule Stabilizer", *Arthritis Rheum.*, vol. 36, No. 9 (Suppl.) 1993, p. 42.

"A Powerful Case for LOPID", Parke–Davis, dated prior to Jan. 8, 1999.

Whitborne, Richard, Ph.D., Presentation at the 2nd International Coronary Stenting Summit (Mar. 1–2, 1991).

SURFACE TREATMENT METHOD FOR STENT COATING

FIELD OF THE INVENTION

The present invention pertains to a medical device having a surface treatment applied over a portion of its surface and methods to eliminate imperfections in the surface treatment. In particular, the present invention is directed to implantable medical devices having drug release coatings including a therapeutic substance in a polymeric carrier and methods to eliminate imperfections in the coating formed during the application of the polymeric material.

BACKGROUND OF THE INVENTION

While angioplasty has gained wide acceptance, abrupt closure and restenosis have been identified as possible subsequent occurrences. Abrupt closure refers to the acute occlusion of a vessel immediately after or within the initial hours following a dilation procedure. Abrupt closure can result in myocardial infarction if blood flow is not restored in a timely manner. The primary mechanisms of abrupt closures are arterial dissection and/or thrombosis. Restenosis refers to the re-narrowing of an artery after an initial successful angioplasty. Restenosis occurs primarily within the initial six months after angioplasty, and is believed due to the proliferation and migration of the cellular components of the arterial wall.

Endovascular stents are placed in the dilated segment of a vessel lumen to mechanically block the effects of abrupt closure and restenosis. In U.S. Pat. No. 5,514,154, Lau et al. disclose an expandable stent which is relatively flexible along its longitudinal axis. This flexibility facilitates delivery of the stent through tortuous body lumens. Additionally, the stent is stiff and stable enough radially, in an expanded condition, to maintain the patency of a body lumen such as an artery when implanted therein. Such stents have not, however, eliminated abrupt closure and have not eliminated restenosis.

Recent developments have led to stents which can provide anti-thrombogenic and other medications to regions of a blood vessel which have been treated by angioplasty or other interventional techniques. In U.S. Pat. No. 5,464,650, Berg et al. disclose a method for making an intravascular stent by applying to the stent, and in particular to its tissue-contacting surface, a solution which includes a solvent, a polymer dissolved in the solvent, and a therapeutic substance dispersed in the solvent. After the solution is applied to the stent, the solvent is then evaporated leaving the polymer/therapeutic agent surface treatment. Berg et al. assert that these devices are capable of providing both short term medication delivery, over the initial hours and days after the treatment, as well as long term medication delivery, over the weeks and months after the treatment.

The process disclosed by Berg et al., which uses a polymeric carrier, is prone to the formation of polymeric surface imperfections during the coating processes. This is especially evident on stents, which generally include many wire like members with interstitial spaces therebetween. The surface imperfections can include strands of drug laden polymeric material hanging loosely from or extending across interstitial spaces between stent portions. The imperfections can also include chunks or thickened coating portions at particular points relative to the rest of the coating. These imperfections, because of their drug delivering capabilities, may cause adverse effects. Loose strands or strands across interstitial spaces may not be secure, and thus, may enter the blood stream and fail to provide local treatment. If these agents are released to locations other than the targeted tissue, unwanted side effects may result. An uneven coating or one with chunks may result in non-uniform treatment of the vessel wall.

SUMMARY OF THE INVENTION

The present invention provides a method for quickly and efficiently eliminating polymeric imperfections on the surface of a medical device coated with such polymeric material, either alone or in combination with a therapeutic substance. In preferred embodiments, the present invention includes an endovascular stent comprising a tubular structure having an initial diameter and being expandable from the initial diameter to an enlarged diameter. The stent further comprises a polymeric surface treatment which is applied to at least a portion of the exterior surface of the tubular structure. The polymeric surface treatment preferably include a matrix of a polymer incorporating a therapeutic agent. With the present method, the stent is first coated with the polymeric surface treatment, followed by contact with a vaporized solvent for a specified time period in order to eliminate the polymeric imperfections formed during the coating procedure. This final procedure thereby adding beneficial characteristics over prior art coated devices carrying a therapeutic substance. Uniform local delivery is assured by eliminating or reducing loose strands or uneven thicknesses of polymer containing the therapeutic substance.

Additional features of the invention and the advantages derived therefrom, and the various scopes and aspects of the invention will become apparent from the drawings, the description of the preferred embodiments of the invention, and the claims.

DETAILED DESCRIPTION OF THE INVENTION

Figure 1:
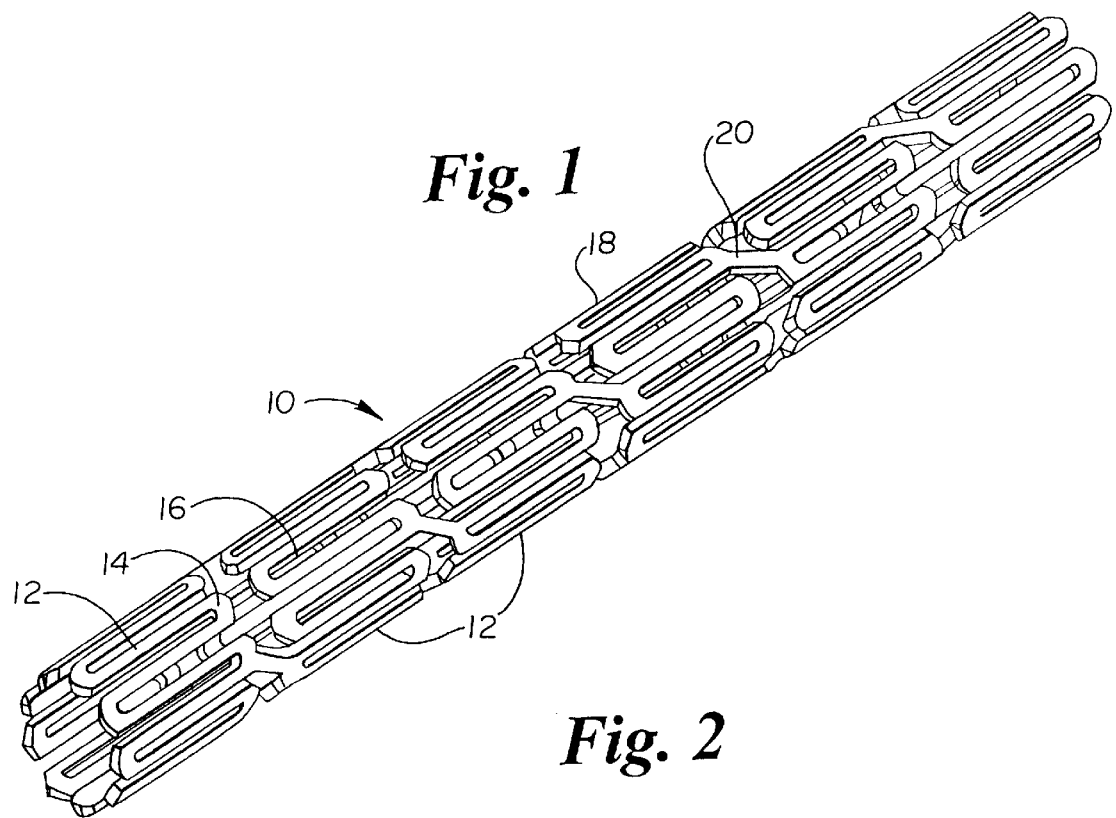
FIG. 1 is a perspective view of a stent in accordance with an exemplary embodiment of the present invention.

Referring now to the drawings wherein like reference numerals refer to like elements throughout the several views, FIG. 1 shows a perspective view of a stent 10, in a non-expanded form, in accordance with the present invention. The skeletal frame of the stent 10 preferably includes wire-like members 12 forming a distinct, repetitive serpentine pattern. This repetitive serpentine pattern consists of multiple U-shaped curves 14. The areas within the U-shaped curves 14 are open 16. With no recognizable beginning or end to this serpentine pattern, wire 12 forms expandable serpentine element 18. Serpentine elements 18 are arranged along the longitudinal axis of the stent 10 so that the U-shaped curves 14 of abutting serpentine elements 16 may be joined through an interconnecting element 20. Through the interconnecting elements 20, a continuous wire 12 framework is created between multiple serpentine elements 18 forming the stent 10.

Figure 2:
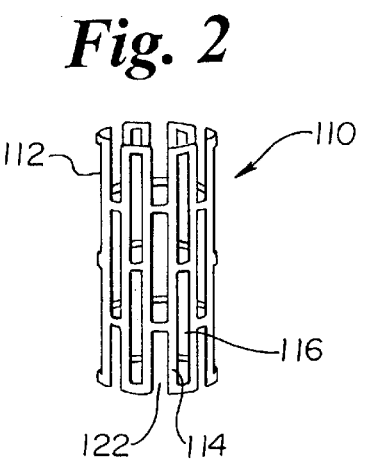
FIG. 2 is a perspective view of a further preferred stent in accordance with the present invention.

FIG. 2 shows a perspective view of a further preferred stent 110 in accordance with the present invention. This stent 110, also has a continuous wire 112 framework. This framework, however, is maintained by a repetitive rectangular-patterned element 114. The areas within the rectangular wire element 114 are open 116. The rectangular wire elements 114 are aligned lengthwise in the longitudinal axis of the stent 110. Adjacent rectangular wire elements 114 are offset half the lengthwise distance of a similar rectangular wire element 114. The end of the stent is formed by the full completion of one rectangular wire element 114, and the subsequent open end of the adjacent rectangular wire element 122. Thus, the ends of the stent possess an alternating open-closed wire configuration.

These stents are exemplary of stents which may incorporate the present invention. These, and other suitable stents are disclosed in U.S. patent application Ser. No. 08/874,190, filed Jun. 13, 1997, now abandoned, entitled "Polymeric Layered Stent", of which the disclosure is incorporated herein by reference.

The term "wire", as used in describing the frame material, should not be mistaken as being limited to metallic materials. In fact, the "wire" forming the stents 10 & 110 may consist of any biocompatable material possessing the structural and mechanical attributes necessary for supporting a diseased vessel. Thus, both metallic and polymeric materials are suitable. Examples of preferred biocompatable metallic materials include stainless steel, tantalum, nitinol, and gold. Preferred polymeric materials may be selected from the list immediately below, which is not exhaustive:

poly(L-lactide) (PLLA), poly(D,L-lactide) (PLA), polyglycolide (PGA), poly(L-lactide-co-D,L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxylbutyrate (PHBT), poly(phosphazene), polyD,L-lactide-co-caprolactone) (PLA/PCL), poly(glycolide-co-caprolactone) (PGA/PCL), polyanhydrides (PAN), poly(ortho esters), poly(phoshate ester), poly(amino acid), poly(hydroxy butyrate), polyacrylate, polyacrylamid, poly(hydroxyethyl methacrylate), polyurethane, polysiloxane and their copolymers.

The skeletal framework of the stents may be formed through various methods as well. The framework may be welded, molded, or consist of filaments or fibers which are wound or braided together in order to form a continuous structure.

Often it is beneficial to both stent and treat the localized area of a diseased vessel. A therapeutic agent, therefore, can be incorporated into a polymer and applied to the stent as a polymeric surface treatment. The incorporation of a therapeutic agent into a surface treatment greatly enhances the scope of this medical device by transforming the stent into a drug-delivery system. Drugs and treatments which utilize anti-thrombogenic agents, anti-angiogenesis agents, anti-proliferative agents, growth factors, and radiochemicals may be readily deployed from within the matrix of the polymeric surface treatment. Specific examples of preferred therapeutic agents include angiopeptin, colchicine, lovastatin, trapidil, ticlopidine, hirudin, Taxol, heparin, and growth factors VEGF, TGF-beta, IGF, PDGF, and FGF.

The application of such a surface treatment is generally accomplished through either a dipping or spraying process. For either process, a solvent carrier is prepared in order to incorporate the therapeutic agent within the polymer matrix. The applied mixture preferably comprises a solvent, a polymer, and a therapeutic agent.

Solvent selection is critical to a functioning surface treatment. It is essential that the solvent is capable of placing the polymer into solution, and that the solvent and polymer chosen do not chemically alter the therapeutic character of the therapeutic agent. On the other hand, the therapeutic agent needs to be dispersed throughout the solvent. The therapeutic agent, therefore, may be either in a true solution with the solvent or dispersed in fine particles within the solvent. Examples of some suitable polymer/solvent/therapeutic agent combinations can include: polylactic acid/trichloroethane/colchicine; polyurethane/tetrahydrofuron/taxol; (PLA/PCL)/dimethylformamide/hirudin; (PLA/PGA)/ethylacetate/ticlopidine; and polyethylene oxide/ethanol/heparin. These combinations are merely exemplary, and it is recognized that other combinations are possible.

As stated earlier, the solution may be applied to the stent 10 by either spraying the stent 10 with, or immersing in, the polymer/solvent/therapeutic agent solution. Whether one chooses application by immersion, or application by spraying, depends principally on the viscosity and surface tension of the solution. It has been found, however, that spraying in a fine spray is preferable. The solution is applied to the stent 10 and the solvent is allowed to evaporate, thereby leaving on the stent surface a coating of the polymer and the therapeutic agent.

Although the procedures for applying the polymeric surface treatments are optimized, they still often leave polymeric fibers, polymeric particles, or other polymeric surface aberrations or imperfections on the stent 10. The goal of this invention is to remove, eliminate or reduce these polymeric imperfections, thereby eliminating the unwanted effects associated therewith.

Figure 3:
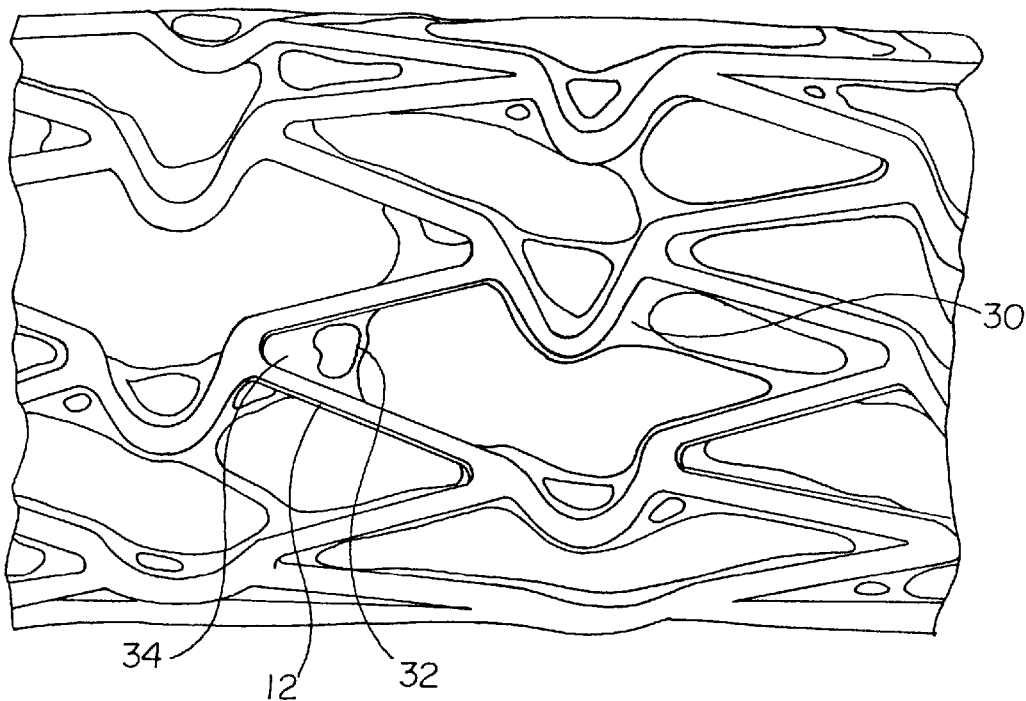
FIG. 3 is a magnified, partial plan view of the stent of FIG. 1, illustrating the polymeric surface aberrations and imperfections arising from a polymeric coating procedure.

FIG. 3 shows a magnified, partial plan view of FIG. 1, illustrating the polymeric surface aberrations and imperfections 30 arising from a polymeric coating procedure. Polymeric imperfections 30 may take-on numerous shapes and sizes. Regardless of the application process utilized, several types of imperfections 30 are common. Examples of these imperfections 30 are polymeric fibers 32 which span the openings 16 of the wire 12 framework, and the overabundance of polymeric material in undesired locations 34. Excess polymeric material 30 is often the result of disproportionate spraying of the polymeric material, or the settling of excessive material in a particular location. At the least, these imperfections 30 are unsightly. More importantly, however, the concern with these imperfections 30 is of possible adverse secondary effects.

The adverse secondary effects which may arise are correlated to the type of polymeric imperfection 30. Polymeric fibers 32, as described earlier, are prone to two adverse effects; the fibers 32 may either dislodge from the stent, or they may release their therapeutic agents into the blood stream. Because polymeric fibers 32 span across the openings 16 of a stent 10, they are attached typically to the stent 10 at few locations. Expansion of the stent 10 may dislodge these imperfections 32, sending them within the circulatory system. At this point, there exists no control over the drug delivering capabilities of these rogue polymeric imperfections 32. The release of drugs in undesired locations is likely to cause secondary effects. On the other hand, the polymeric fiber 32 may remain attached to the stent 10. The imperfection 32, however, may span across an opening 16 which does not engage a vessel wall. In this instance, the polymeric imperfection 32 may release its therapeutic agent directly into the blood stream, causing other secondary effects.

Polymeric imperfections 30 caused by an overabundance of polymeric material 34 may also cause secondary effects. The goal of applying a polymeric surface treatment upon a stent 10 is to have uniform coverage and uniform release of a therapeutic substance. When there are areas of excess coverage on the stent 10, the polymeric material 34 may contact the vessel wall unevenly. This uneven contact subsequently causes the targeted diseased tissue to receive varying doses of the released therapeutic agents. For therapeutic agents, especially ones which promote or restrict endothelial cell growth, the uneven contact and subsequent drug release may cause less than optimal treatment. Another problem associated with this type of polymeric imperfections 34 is, like the polymeric fibers 32, that the imperfections 34 may not contact the vessel wall in any form. In this case, the therapeutic agent may be released directly into the blood stream causing other secondary effects to arise.

By contacting the coated stent 10 having these polymeric imperfections 30 with a vaporized solvent 40, these imperfections 30, and the adverse effects associated with them, are eliminated. Most importantly, these polymeric imperfections 30 are eliminated without abrogating the integrity of the surface coating over the remaining portions of the stent 10. When the stent 10 is applied with the polymer/solvent/ therapeutic agent solution, the solution dries leaving a therapeutic agent incorporated within a polymeric matrix. Depending upon the solution used, the imperfections 30 may be removed after, or prior to the drying of the solution. At this stage, the stent 10 is contacted with a vaporized solvent 40 for a predetermined time period. This time period is highly dependent upon the solution forming the surface treatment and the solvent used. In general, the time period varies from about 0.5 seconds to about 2 hours, with a preferred time of about 1 second to about 10 minutes and a most preferred range of about 10 seconds to 1 minute.

The vaporized solvent 40 utilized is also highly dependent upon the solution, including the polymer, used to form the surface treatment. Typically, the vaporized solvent 40 will be organic. Examples of suitable organic solvents include hydrocarbons, halocarbons, polyethers, cyclic ethers, alkyl amids, ethyl acetate, benzene, alkyl-substituted benzene derivatives, and alcohols. Additionally, the vaporized solvent 40 may be a combination of any of the organic solvents listed.

In preferred practice the present invention, coated stents are simply placed within a chamber containing a vaporized solvent. Contact time is adjusted, depending upon the degree of aberrations to be removed. The chambering may be any container, but is preferably a closed container having liquid solvent present in the bottom. This solvent vaporizes to a degree to which the solvent reaches equilibrium based on temperature and pressure within the container. The stent or stents to be treated are suspended within the vapor space of the container so that vaporized solvent contacts the surface imperfections. Preferably, the container allows viewing of the stent during treatment so that the progress of removing imperfections can be monitored. It is, however, recognized that other apparatus may be utilized so long as the surface imperfections are placed in contact with the solvent vapor or liquid.

Figure 4:
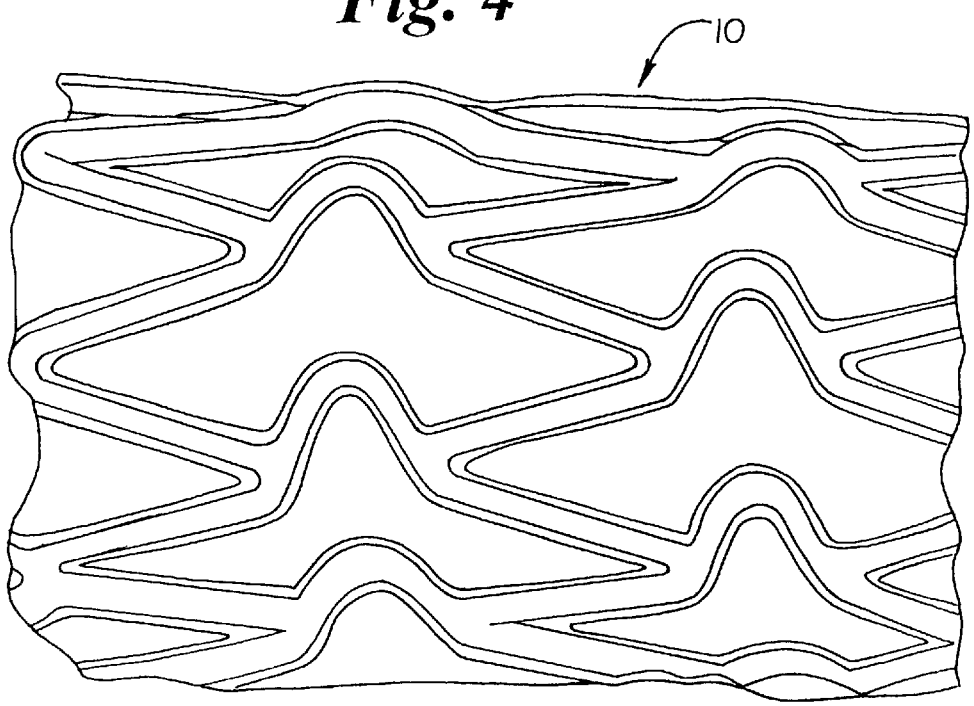
FIG. 4 is the magnified, partial plan view of FIG. 3, after contacting the stent with a preferred embodiment of vaporized solvent.

FIG. 4 is the magnified, partial plan view of FIG. 3, after contacting the stent with a preferred embodiment of vaporized solvent. As evidenced in the figure, surface irregularities have been eliminated.

Numerous characteristics and advantages of the invention covered by this document have been set forth in the foregoing description. It will be understood, however, that this disclosure is, in many aspects, only illustrative. Changes may be made in details, particularly in matters of shape, size, and arrangement of parts without exceeding the scope of the invention. The invention's scope is defined, of course, in the language in which the appended claims are expressed.

What is claimed is:

1. A method for eliminating polymeric fibers, polymeric particles or other polymeric surface aberrations or imperfections from a polymeric coating on a medical device, the method comprising the steps of:

providing a medical device having a surface generally defined by a skeletal frame having spaces therebetween, wherein at least a portion of said surface is coated with a polymeric material, some of said polymeric material extending across said spaces; and, contacting said polymeric coating with a vaporized solvent, thereby eliminating said polymeric material extending across said spaces.

2. The method of claim 1, wherein said polymeric material is at least partially soluble in said vaporized solvent.

3. The method of claim 2, wherein said polymeric material is contacted with said vaporized solvent for between about 0.5 seconds to about 2 hours to thereby eliminate surface fibers, surface particles or other surface aberrations without abrogating the integrity of said polymeric coating over said surface.

4. The method of claim 2, wherein said vaporized solvent is an organic solvent.

5. The method of claim 4, wherein said organic solvent is selected from the group consisting of hydrocarbons, polyethers, halocarbons, alkyl amides, cyclic ethers, ethyl acetate, benzene, alkyl-substituted benzene derivatives, alcohols, and combinations thereof.

6. The method of claim 1, wherein said polymeric coating is selected from the group consisting of polyethylene oxide (PEO), polylactic acid, polyglycolic acid, polycaprolactone, polyurethane, polysiloxane and their copolymers.

7. The method of claim 1, wherein said polymeric coating includes a therapeutic agent releasably incorporated therein.

8. The method of claim 7, wherein said therapeutic agent is selected from the group consisting of an anti-thrombogenic agent, an anti-angiogenesis agent, heparin, hirudin, ticlopidine, and Taxol.

9. The method of claim 1, wherein said contact between said polymeric coating and said vaporized solvent occurs through a dipping process.

10. The method of claim 1, wherein said contact between said polymeric coating and said vaporized solvent occurs through a spraying process.

11. A method of coating a medical device with a polymeric material wherein said coating is generally free of polymeric strands, polymeric particles or other polymeric surface aberrations, said method comprising the steps of:

providing a medical device having a surface generally defined by a plurality of interconnected stunts with open interstitial spaces therebetween, coating at least a portion of said surface with a polymeric material in a solvent carrier;

drying said polymeric material by evaporating at least a portion of said solvent carrier to form a dried polymeric coating, wherein some of said dried polymeric material extends across said interstitial spaces; and, contacting said dried polymeric coating with a vaporized solvent, thereby eliminating said polymeric material extending across said interstitial spaces.

12. The method of claim 11, wherein said polymeric material is contacted with said vaporized solvent for between about 0.5 seconds to about 2 hours to thereby eliminate surface fibers, surface particles or other surface aberrations without abrogating the integrity of said polymeric coating over said surface.

13. The method of claim 11, wherein said vaporized solvent is an organic solvent.

14. The method of claim 13, wherein said organic solvent is selected from the group consisting of hydrocarbons, polyethers, cyclic ethers, ethyl acetate, benzene, alkyl-substituted benzene derivatives, alcohols, and combinations thereof.

15. The method of claim 11, wherein said polymeric coating is selected from the group consisting of polyethylene oxide (PEO), polylactic acid, polyclycolic acid, and polycaprolactone, polyurethane, polysiloxane and their copolymers.

16. A method for coating a stent with a polymeric material having a therapeutic substance dispersed therein for timed release of said therapeutic substance when said stent is implanted wherein said coating is generally free of polymeric strands, polymeric particles or other polymeric surface aberrations, said method comprising the steps of:

providing a stent having a surface generally defined by a plurality of interconnected struts with open interstitial spaces therebetween;

coating at least a portion of said surface with a polymeric material in a solvent carrier;

drying said polymeric material by evaporating at least a portion of said solvent carrier to form a dried polymeric coating, wherein some of said dried polymeric material extends across said interstitial spaces; and, contacting said dried polymeric coating with a vaporized solvent, thereby eliminating said polymeric material extending across said interstitial spaces.

17. The method of claim 16, wherein said polymeric material is at least partially soluble in said vaporized solvent.

18. The method of claim 17, wherein said polymeric material is contacted with said vaporized solvent for between about 0.5 seconds to about 2 hours to thereby eliminate surface fibers, surface particles or other surface aberrations without abrogating the integrity of said polymeric coating over said surface.

19. The method of claim 17, wherein said vaporized solvent is an organic solvent.

20. The method of claim 19, wherein said organic solvent is selected from the group consisting of hydrocarbons, polyethers, halocarbons, alkyl amides, cyclic ethers, ethyl acetate, benzene, alkyl-substituted benzene derivatives, alcohols, and combinations thereof.

21. The method of claim 16, wherein said polymeric coating is selected from the group consisting of polyethylene oxide (PEO), polylactic acid, polyglycolic acid, polycaprolactone, polyurethane, polysiloxane, and their copolymers.

22. The method of claim 16, wherein said contact between said polymeric coating and said vaporized solvent occurs through a dipping process.

23. The method of claim 16, wherein said contact between said polymeric coating and said vaporized solvent occurs through a spraying process.

24. The method of claim 16, wherein said therapeutic substances include anti-proliferative agents, anti-thrombogenic agents, or a combination thereof.

25. The method of claim 16, wherein said therapeutic substance in said polymeric material is contacted with said vaporized solvent.

* * * * *

UNITED STATES PATENT AND TRADEMARK OFFICE
CERTIFICATE OF CORRECTION

PATENT NO. : 6,120,847
DATED : September 19, 2000
INVENTOR(S) : Dachuan Yang et al.

It is certified that error appears in the above-identified patent and that said Letters Patent is hereby corrected as shown below:

Title Page,

Inventors: delete "Jacob" and insert –Iacob--.

Column 6, claim 11, line 55, delete "stunts" and insert –struts--.

Signed and Sealed this

Fifteenth Day of May, 2001

*Attest:*

NICHOLAS P. GODICI

*Attesting Officer*     *Acting Director of the United States Patent and Trademark Office*